United States Patent [19]

Fleck et al.

[11] 3,996,210
[45] Dec. 7, 1976

[54] MONOBENZOXAZOLYLSTILBENES

[75] Inventors: Fritz Fleck; Salvatore Valenti, both of Bottmingen, Switzerland

[73] Assignee: Sandoz Ltd., Basel, Switzerland

[22] Filed: June 8, 1970

[21] Appl. No.: 44,659

[30] Foreign Application Priority Data

June 13, 1969 Switzerland .................. 9052/69

[52] U.S. Cl. .................. 260/240 CA; 252/301.24; 252/543; 427/158

[51] Int. Cl.² ...................................... C07D 263/56

[58] Field of Search ........................... 260/240 CA

[56] References Cited

FOREIGN PATENTS OR APPLICATIONS 1,378,454 10/1964 France .................. 260/240 CA
1,378,455 10/1964 France .................. 260/240 CA

OTHER PUBLICATIONS

Netherlands Published Application, published May 2, 1967, Application by Ciba Ltd. 116 pages and 22 pages dwgs, pp. 1–7, 11, 23–24 and 1 sheet dwgs. containing figure 239 relied upon.

*Primary Examiner*—John D. Randolph
*Attorney, Agent, or Firm*—Gerald D. Sharkin; Richard E. Vila; Thomas C. Doyle

[57] ABSTRACT

Monobenzoxazolylstilbenes of formula

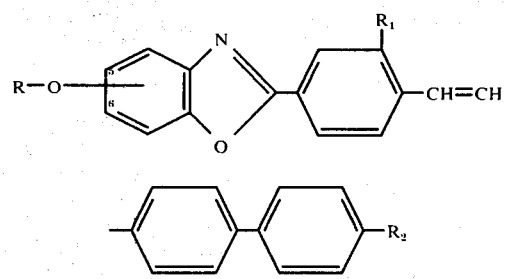

wherein
R—O is lower alkoxy and stands in one of the positions 5 or 6,
$R_1$ is hydrogen or lower alkyl and
$R_2$ is hydrogen, chlorine or lower alkyl.

7 Claims, No Drawings

MONOBENZOXAZOLYLSTILBENES

This invention relates to new monobenzoxazolylstilbenes of formula

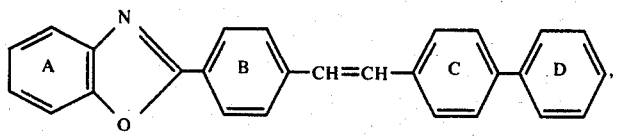

where the benzene nucleus A bears, preferably in the 5- or 6-position, at least one hydrocarbon radical bound through an oxygen atom and the benzene nuclei A, B, C and D, independently of each other, may bear halogen atoms such as chlorine or bromine atoms and alkyl or alkoxy radicals, preferably lower alkyl or alkoxy radicals.

Especially noteworthy are the compounds of formula

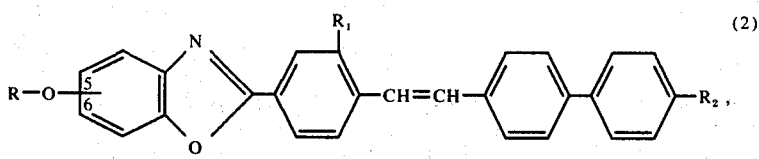

where
R stands for an aliphatic hydrocarbon radical which bears 1 to 4 carbon atoms and may be substituted,
$R_1$ for hydrogen or alkyl which bears 1 to 4 carbon atoms, preferably methyl,
$R_2$ for hydrogen, halogen, preferably chlorine, or alkyl with 1 to 4 carbon atoms, preferably methyl,
and where the radical R—O— is bound in the 5- or 6-position of the benzoxazole radical.

One process of production for the compounds of formula (I) consists in the acylation of an aminophenol of formula

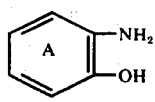

or a salt of such an aminophenol, with a stilben-monocarboxylic acid of formula

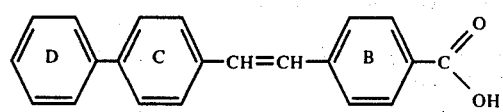

where A, B, C and D have the aforestated meanings, or with one of the functional derivatives of such an acid, for instance the anhydride or a halide such as the chloride, ester or nitrile, followed by cyclization of the resulting amide at high temperature and preferably in the presence of an acid condensing agent.

A second process of production consists in the condensation of a compound of formula

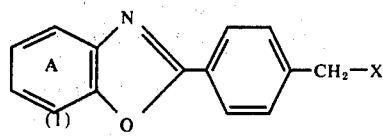

where
X represents —H, —COOH, —COO—alkyl, —CN or —PO(O—lower alkyl)$_2$,
with a p-diphenylaldehyde of formula

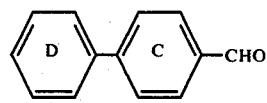

or a functional derivative of such an aldehyde, such as an oxime, hydrazone or anile, in the presence of a suitable catalyst such as boric acid, zinc chloride, arylsulphonic acids, such as benzene- or 4-methylbenzenesulphonic acid, alkali salts or alkaline earth salts of arylsulphonamides, such as the sodium, potassium, calcium or barium salts or benzene- or 4-methylbenzenesulphonamide, acetic anhydride, alkali acetates, such as sodium or potassium acetate, pipiridine, alkali or alkaline earth hydroxides or alkali or alkaline earth alcoholates, such as the hydroxides or alcoholates of sodium, potassium, calcium or barium, with subsequent elimination of the group X by a suitable method, provided it has not been split off in the condensation reaction. In the formulae (5) and (6) the letters A, B, C and D have the meanings given in the foregoing.

The following compounds may be cited as examples of o-aminohydroxybenzenes of formula (3):
1-amino-2-hydroxyalkoxybenzenes in which the alkoxy group has preferably not more than 4 carbon atoms, e.g.
  1-amino-2-hydroxy-4-methoxybenzene hydrochloride,
  1-amino-2-hydroxy-5-methoxybenzene hydrochloride,
  1-amino-2-hydroxy-6-methoxybenzene hydrochloride;
1-amino-2-hydroxyalkylalkoxybenzenes in which each alkyl and alkoxy radical has preferably not more than 4 carbon atoms, e.g.:
  1-amino-2-hydroxy-4-methoxy-5-methylbenzene hydrochloride;
1-amino-2-hydroxydialkoxybenzenes in which each alkoxy group has preferably not more than 4 carbon atoms, e.g.

1-amino-2-hydroxy-4,5-dimethoxybenzene hydrochloride, 1-amino-2-hydroxy-4,6-dimethoxybenzene hydrochloride.

The p-diphenylaldehydes of formula (6) may be the following compounds :

2-chloro-4-phenylbenzaldehyde,
4-(p-methylphenyl)-benzaldehyde
4-(p-methoxyphenyl)-benzaldehyde
4-(p-chlorophenyl)-benzaldehyde
p-phenylbenzaldehyde or similar compounds.

The compounds of formula (4) employed as starting products can be prepared, for example, by condensation of a p-diphenylaldehyde of formula (6) with p-toluic methylester, if necessary with subsequent saponification of the ester group in the condensation product and reaction of the carboxyl group with thionyl chloirde.

Compounds of formula (5) are obtainable by condensation of an aminophenol of formula (3) with a substituted or unsubstituted p-toluic chloride by the aforestated methods, followed by suitable substitution of the methyl group.

The reaction of the aminophenols of formula (3) with a stilbenemonocarboxylic acid of formula (4) or one of its functional derivatives can be conveniently effected at room temperature to 350° C. The reaction can be carried out at room temperature to 150° C when a halide or anhydride of a stilbenemonocarboxylic acid of formula (4) is employed, or at 100° to 200° C when the free acid, the nitrile or a lower alkyl ester such as the methyl or ethyl ester is used. It is preferable to effect acylation in the presence of an inert organic solvent and in an inert gas atmosphere, e.g. under nitrogen, and then to carry out cyclization at 150° to 350° C, preferably at 160° to 280° C, in the presence of an acid catalyst and an inert organic solvent of high boiling point in an inert gas atmosphere, e.g. nitrogen.

The suitable solvents for acylation include aromatic aliphatic and cycloaliphatic hydrocarbons which may be halogenated or nitrated, e.g. alkanes, or preferably alkane mixtures with boiling points from 80° to 250° C, 1,2-dichlorethane, 1,1,2,2-tetrachlorethane, carbon tetrachloride, nitromethane, nitroethane, benzene, toluene, xylene, alkylbenzene mixtures, chlorobenzene, ortho-dichlorobenzene, trichlorobenzenes, 2- and 4-chlorotoluene, nitrobenzene, 2-nitrotoluene, cyclohexane, methylcyclohexane, ethers, e.g. 1,2-dimethoxy-, 1,2-diethoxy- and 1,2-di-(n-butoxy)ethane, dioxan, methoxybenzene, ethoxybenzene, acid amides, e.g. dimethylformamide, diethylformamide, dimethylacetamide, N-methylpyrrolidone, phosphoric acid-tris-(dimethylamide), sulphoxides, sulphones, e.g. dimethyl sulphoxide, dimethyl sulphone and tetramethylene sulphone. If the halides of stilbenemonocarboxylic acids are employed the liberated hydrogen halide can be eliminated with the aid of a stream of dry nitrogen, but often it is more convenient to add an inert tertiary amine to bind the freed hydrogen halide, or to carry out acylation in an inert tertiary amine.

Examples of tertiary amines suitable for this purpose are N,N-dimethylamino- and N,N-di-ethylamino-benzene, triethylamine, tri-(n-butyl)-amine, pyridine, the picolines, quinoline and mixtures of pyridine bases.

The acylation product can be isolated by filtration if it is in suspension, or by precipitation with a suitable agent and filtration, or again by evaporation or steam distillation of the solvent and filtration, after which cyclization is carried out as a separate operation.

Inert organic solvents with boiling points above 150° C and preferably at 200° C or higher are used for cyclization, for example otho-dichlorobenzene, trichlorobenzene mixtures, nitrobenzene, bis-(ethoxyethyl)-ether, bis-(n-butoxyethyl)-ether, tetramethylene sulphone. An acid condensing agent is added for cyclization, for example boric acid, boric anhydride, boric trifluoride, boric trifluoride etherate, zinc chloride, aromatic or aliphatic sulphonic acids, e.g. benzene-, 4-methylbenzene-, methane- or ethanesulphonic acid, polyphosphoric acid, pyrophosphoric acid, phosphorus trichloride, phosphorus oxychloride. It is best to employ the phosphoric acids in amounts of about 5–10 % by weight on the total weight of the reactants.

If the reaction is carried out in the presence of boric acid, zinc chloride, a phosphorus chloride or one of the aforenamed sulphonic acids as condensing agent, it is advisable to employ this agent in catalytic amounts, e.g. 0.5–5 % on the total weight of the reactants. If smaller amounts, e.g. 0.1 %, are used the rate of reaction is much slower, while greater amounts, e.g. 10 %, produce no appreciable improvement. If acylation and cyclization are conducted without isolation of the intermediate, it is preferable to work first at temperatures of 100° to 200° C and then in the temperature range of 150° to 280° C, in the presence of one of the aforenamed acid condensing agents and an inert organic solvent of high boiling point.

The benzoxazolylstilbenes can be isolated in the manner described for the intermediates.

The reaction of a p-diphenylaldehyde of formula (6) or one of its functional derivatives such as the oxime, hydrazone or anile with a compound of formula (5) is accomplished in the presence of one of the aforestated catalysts at temperatures ranging from 0° to 200° C, preferably from 20° to 170° C. Subsequently the group X, if present, is removed by a suitable method.

The reaction can be carried out by melting the reactants, or more advantageously in an inert solvent, for example an aliphatic or aromatic, preferably halogenated hydrocarbon, an alcohol, an ether, a glycol, an amide such as formamide, dimethyl formamide or dimethyl acetamide, N-methylpyrrolidone, phosphoric acid-tris(dimethylamide), acetonitrile, dimethylsulphoxide or tetramethylenesulphone.

The compounds of formula (1) can be isolated by the normal methods, e.g. by filtration with suction if present in suspension, by precipitation with a suitable agent and filtration with suction, by evaporation or steam distillation of the solvent and filtration with suction of the precipitated product.

The new monobenzoxazolylstilbenes of formula (1) have excellent properties for the optical brightening of the most varied organic materials and plastics. By "organic materials" are understood natural fibres such as cotton and wool, and more especially synthetic fibre-forming polymers such as polyesters, polyamides, polyurethanes, polyolefines (polyethylene, polypropylene), polyvinyl acetate, polyvinyl chloride, polyvinylidene chloride, polyacrylonitrile, modified polyacrylonitrile, cellulose triacetate, secondary cellulose acetate and polystyrene. These materials may be present in any of the forms occurring in manufacture and in any state of distribution. Thus the compounds of formula (1) can be added to, or incorporated in, the materials before or during the process of conversion into their final form For instance, they can be added to the mass for the production of plastic film or sheet or moulded articles, or they can be dissolved or finely dispersed in the solutions or melts for spinning filaments.

The monobenzoxazolylstilbenes conforming to this invention can be added with good success to the monomers or monomer precondensates for the synthesis of synthetic polymers. If they are employed for brightening textiles they can be applied from solution in a solvent or in finely dispersed form, e.g. from aqueous dispersion. If the compounds are employed to brighten polyester or polyester blend fabrics, padding from aqueous dispersion, drying and thermofixation is a highly suitable method of application. Finally, the compounds can be fixed on a carrier material in a fine state of division and applied in this form to brighten further substrates.

The compounds of formula 1) are employed in amounts of 0.001 to 0.5 % in relation to the weight of the material for brightening, the exact addition depending on the method of application. They can be applied singly or in combination with other brighteners, and in the presence of chemical bleaching agents and/or surface-active agents such as detergents and carriers.

On organic materials these brighteners produce excellent neutral blue to violet-blue fluorescence. The brightening effects are very fast to light, stable to heat and resistant to bleaching agent solutions.

Other monobenzoxazolylstilbenes have been described for use as optical brightening agents, for instance in French Pat. Nos. 1,378,455, 1,293,281 and 1,499,546. A great number of these compounds, however, are technically uninteresting because of inadequate effectiveness and moderate light fastness. In intensity of fluorescence 4'-phenyl-substituted 4-benzoxazolylstilbenes behave somewhat better, but they have relatively high melting points and poor solubility in organic materials, which renders difficult their incorporation in these materials.

It has now been found, unexpectedly, that by introducing alkoxy groups into the benzoxazolyl radical of the aforesaid 4'-phenyl-4-benzoxazolylstilbenes, more especially in the 5- and 6-positions, the melting point is reduced and the effectiveness of the compounds greatly increased, while their light fastness on the substrate is enhanced. The improvement in these properties was not foreseeable because the presence of alkoxy groups in monoazolylstilbenes not bearing the 4-phenyl radical, especially if these groups are on the stilbene radical, normally increases the melting point and the ultra-violet absorption relative to the starting compound, and consequently their effectiveness and light fastness are inferior.

The superiority of the brighteners of this invention to the known brighteners is evident from the comparative determinations described below.

COMPARATIVE DETERMINATIONS

The following compounds were applied as optical brighteners:

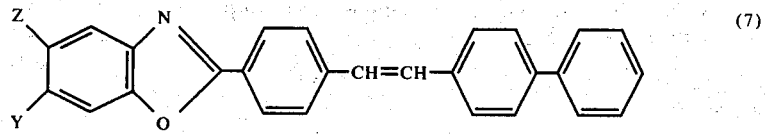

(7)

| Compound | Z | Y |
|---|---|---|
| A | H | H |
| B | OCH₃ | H |
| C | H | OCH₃ |

Compound A is described in Example 18 of French Pat. No. 1,499,546. Compounds B and C are new and form part of the present disclosure.

The three products were incorporated in polyamide, polyester and polypropylene in accordance with the applicaton examples of this disclosure and the polymers were moulded as tiles. The whiteness values of the tiles were determined by fluorimetry using the fluorimeter of the firm Schildknecht, Zurich, Switzerland. The results are listed in the following table, with the percentage weights of the three products in the top horizontal column.

Table

| Substrate | | Polyamide | | | | Polyester | | | | Polypropylene | | | |
|---|---|---|---|---|---|---|---|---|---|---|---|---|---|
| Compound | m.p. | 0.01 | 0.02 | 0.04 | 0.06 | 0.01 | 0.02 | 0.04 | 0.06 | 0.0025 | 0.005 | 0.01 | 0.02 |
| A | 276.5° | 81 | 90 | 99 | 101 | 84 | 101 | 115 | 123 | 39 | 49 | 56 | 59 |
| B | 236° | 106 | 112 | 119 | 123 | 87 | 104 | 120 | 127 | 43 | 54 | 64 | 71 |
| C | 236° | 100 | 110 | 114 | 119 | 89 | 109 | 127 | 134 | 49 | 57 | 68 | 72 |

These comparative determinations show clearly the superiority of the compounds of the present invention. If the effectiveness of compounds A, B and C on a given material at the same concentration is compared, it will be seen that the fluorimetric values are invariably higher for B and C than for A. The comparison is yet more striking when the values are viewed in relation to the amounts of the compounds which have to be used to reach a particular flourimetric value. Thus compound A has to be applied at a concentation of 0.06 % in polyamide to give a fluorimetric value of 101, while B on the same substrate attains to a value of 106 at a concentration of no more than 0.01 %. The yield of compound B on polyamide is thus more than six times greater than that of compound A.

A visual evaluation of A on the one hand and B and C on the other works out yet more favourably for the disclosed compounds. Visual scrutiny of brightened test specimens reveals that the latter compounds impart a higher degree of whiteness, together with greater brilliance and a more neutral shade.

Similar results are obtained when the compounds of this invention are compared against compound A in other materials such as secondary cellulose acetate, polyvinyl chloride and polystyrene, or in spun fibres formed with any of the aforenamed materials. The effects obtained with the new brighteners on polyamide, polyester and polypropylene are, however, worthy of special mention as they are of outstanding quality. The fastness properties of the compounds of this invention are equal or superior to those of the known compounds.

In the following Examples the parts and percentages, unless otherwise stated, are by weight. The temperatures are given in degrees centigrade.

is obtained in good yield and can be reacted further without special purification.

A mixture of 20.0 parts of the compound of formula (9), 1.0 part of boric acid and 100.0 parts by volume of trichlorobenzene is raised to the boil and reacted at this temperature for 6 hours with stirring in the absence of air, during which time the trichlorobenzene distils off almost completely. While the reaction mixture is cooling it is diluted with 120.0 parts by volume of methanol. When it reaches about 5° the precipitate is filtered off with suction, washed with cold methanol and dried. The 4-(5''-methoxybenzoxazolyl-2'')-4'-phenylstilbene of formula

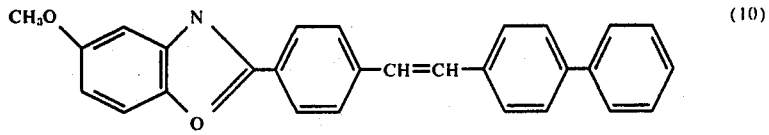

(10)

EXAMPLE 1

A mixture of 50.0 parts of the compound of formula

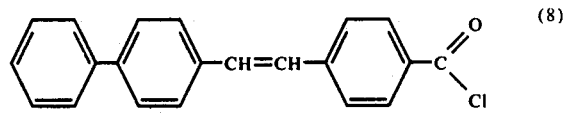

(8)

and 27.5 parts of 1-amino-2-hydroxy-5-methoxybenzene hydrochloride in 220.0 parts by volume of pyridine is reacted with heating in the absence of air for 4 hours with reflux condensing. Subsequently the mixture is cooled to room temperature and run into a mixture of ice and water, on which the product settles out. It is filtered off with suction, washed well with water and dried. The compound of formula is obtained in very good yield in the form of a yellow powder, which after recrystallization from chlorobenzene has a melting point of 235°–236°.

In place of the 27.5 parts of 1-amino-2-hydroxy-5-methoxybenzene hydrochloride, 27.5 parts of 1-amino-2-hydroxy-4-methoxybenzene hydrochloride can be used, with which the 4-(6''-methoxybenzoxazolyl-2'')-4'-phenylstilbene of formula

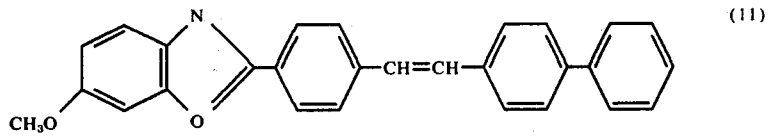

(11)

is obtained in comparably good yield as a yellow powder. It crystallizes from solution in chlorobenzene as yellow scales which melt at 235°–236°.

The 27.5 parts of 1-amino-2-hydroxy-5-methoxybenzene hydrochloride can be replaced by 29.5 parts of 1-amino-2-hydroxy-5-ethoxybenzene hydrochloride or 34.2 parts of 1-amino-2-hydroxy-5-(n-butoxy)-benzene hydrochloride, which are reacted in a fully analogous manner to yield, respectively, the compounds

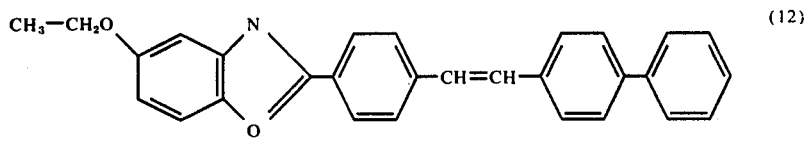

(12)

melting point 214–217° and

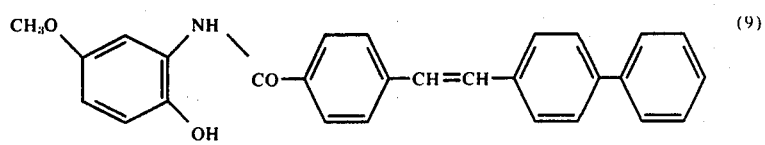

(9)

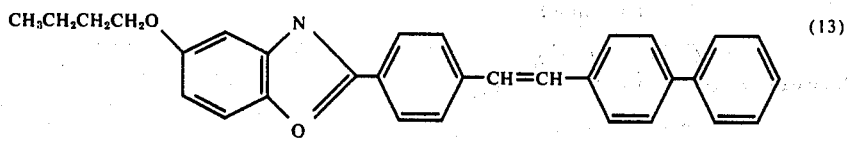

melting point 208–10°

The intermediate of formula (8) can be prepared as follows. A solution of 45.0 parts of the compound of formula

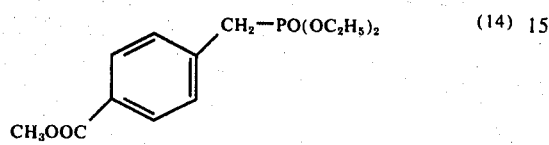

is prepared in 132.0 parts by volume of dimethyl formamide, and to it are added with stirring 9.4 parts of sodium methylate followed by a solution of 28.7 parts of p-phenylbenzaldehyde in 100.0 parts by volume of dimethyl formamide. During addition care is taken to keep the temperature between 25° and 40°. Then the mixture is heated to the boil and stirring is continued for 4 hours at the boil after which the reaction mixture is cooled to about 10° and run into a mixture of water and ice. The produce settles out and is washed well with water and dried. The ester of formula

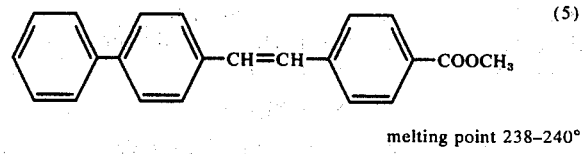

melting point 238–240° is obtained in good yield and can be reacted further without special purification.

17 Parts of the ester of formula (15) are heated in 380 parts by volume of dioxan until all is dissolved. After the addition of 30 parts of water and 10 parts of sodium hydroxide a white precipitate is formed. The mixture is raised to the boil and held at the boil for 6 hours. On cooling the mixture is poured into 1300 parts of water. The mixture is acidified with 20 parts by volume of concentrated hydrochloric acid. The precipitate is filtered off with suction, washed well with cold water and dried.

The compound of formula

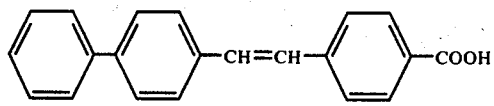

is obtained in almost quantitative yield. Its melting point is higher than 330°. Without further purification it is boiled in 5 times the amount of thionyl chloride for 2 hours 30 minutes with reflux cooling. The thionyl chloride is then completely eliminated with the aid of benzene, leaving as residue the compound of formula (8), which can be reacted further as described above without special purification.

EXAMPLE 2

A mixture of 24.0 parts of the compound of formula

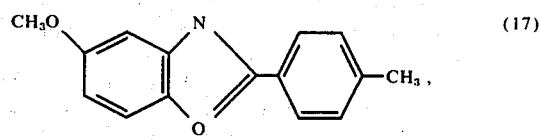

25.8 parts of p-phenylbenzaldehyde-anile and 50.0 parts of potassium hydroxide powder in 600.0 parts by volume of dimethyl formamide is raised to 60° in 30 minutes with stirring and in the absence of air. It is maintained at this temperature for a further 30 minutes, after which it is cooled to about 10°. At a temperature between 10° and 20° 20 parts of water and then 500.0 parts by volume of 10 % hydrochloric aacid are added. The precipitated product is filtered off with suction, washed with water until neutral and dried. The 4-(5''-methoxybenzoxazolyl-2'')-4'-phenylstilbene of formula (10) is obtained in very good yield. It can be purified as described above.

In place of the 2-(4'-methylphenyl)-5-methoxybenzoxazol of formula (17), the 2-(4'-methylphenyl)-6-methoxybenzoxazol of formula

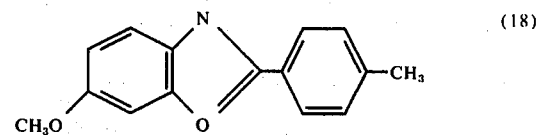

can be employed to yield the 4-(6''-methoxybenzoxazolyl-2'')-4'-phenylstilbene of formula (11), which is obtained in comparably good yield and can be purified as given in the foregoing.

The following compounds can be produced in an analogous manner :

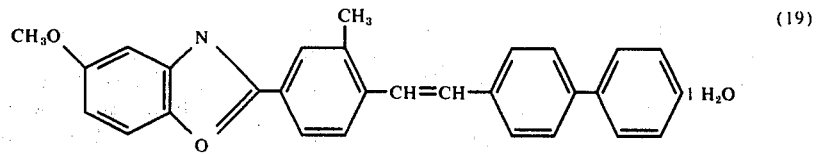

melting point 248–253°

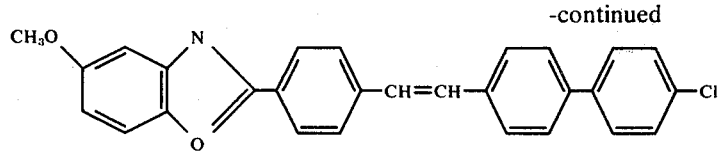

(20)

melting point 262–4°

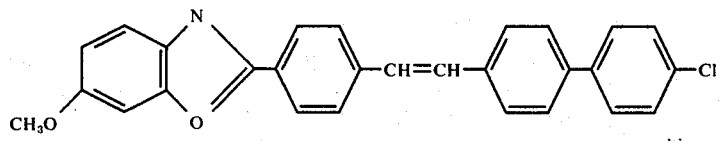

(21)

melting point 154–6°

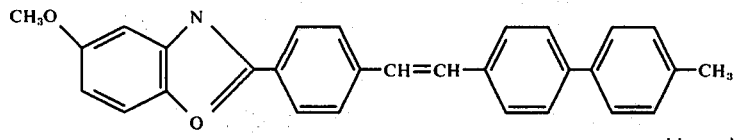

(22)

melting point 185–6°

The intermediate of formula (17) can be produced as follows: A mixture of 10.0 parts of 1-amino-2-hydroxy-5-methoxybenzene hydrochloride and 8.9 parts of p-toluic acid chloride in 80.0 parts by volume of pyridine is heated for 4 hours in the absence of air with reflux condensing. The reaction mixture is cooled and unloaded into a ice-water mixture, the precipitated product filtered off with suction, washed well with water and dried.

The compound of formula

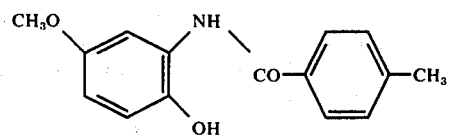

(23)

is obtained in very good yield. It can be crystallized from methanol, on which it melts at 172°–174°.

10.0 Parts of the compound of formula (23) and 1.0 part of boric acid are reacted for 6 hours at 240°–245° in the absence of air, the separated water being continuously distilled during the reaction. The melted mass is cooled and recrystallized from methanol. The compound of formula (17) is obtained in very good yield with melting point 114°.

Replacement of the 10.0 parts of 1-amino-2-hydroxy-5-methoxybenzene hydrochloride by 10.0 parts of 1-amino-2-hydroxy-methoxybenzene hydrochloride yields in a fully analogous manner the compound of formula

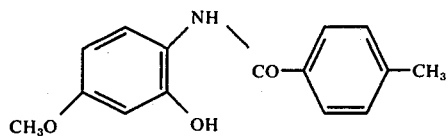

(24)

with melting point 162°–164° (from methanol) and the compound of formula (18) with melting point 84°.

The intermediates of formulae (17) and (18) respectively can be produced as follows.

17.7 Parts of 1-amino-2-hydroxy-5-methoxy or 1-amino-2-hydroxy-4-methoxybenzene are suspended in 230.0 parts by volume of trichlorobenzene. 19.8 Parts of p-toluic acid chloride and 15.7 parts of N,N-dimethylaniline are added. The mixture is held at 130° for 3 hours with stirring and in the absence of air, and then for 1 hour at 160°. After the addition of 1.3 parts of boric acid the temperature is increased to about 200°–210° and this temperature is maintained for 2–3 hours, during which time the solvent distils off almost completely. The reaction mixture is cooled to about 60° and 245.0 parts of methanol are added. It is then brought to the boil, decolourized with charcoal and cooled to about 5°. The product settles out and is filtered off with suction and dried. The compound of formula (17) or (18) respectively is obtained, which requires no further purification.

EXAMPLE 3

38.2 Parts of the compound of formula (17) are dissolved in 180 parts of hot chlorobenzene. A solution of 25.4 parts of bromine in 70 parts of chlorobenzene is added for bromination of the compound, which is conducted with continued heating and reflux cooling and with stirring and ultra-violet radiation, with care taken to maintain a weak reflux. After the bromine addition the mixture is held at the boil for 2 hours, i.e. until the evolution of hydrogen bromide is complete, after which 250 parts by volume of light benzine are added for dilution. The reaction mixture is then cooled, the precipitate filtered off with suction and dried. The compound of formula

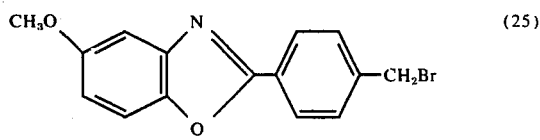

(25)

is obtained in good yield. On purification from light benzine its melting point is 153°–154°.

32.0 Parts of the compound of formula (25) are dissolved with heating in the minimum necessary amount of benzene. The warm solution is gradually added to 20.0 parts of triethyl phosphite at 140°. The benzene and the ethyl bromide formed are distilled over a column. The residue is held at 180° for 2 hours and then distilled under reduced pressure. The compound of formula

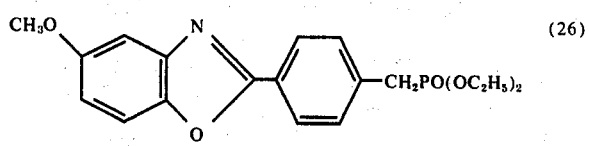

is obtained in very good yield as a colourless oil of thick consistency which requires no further purification.

40.0 Parts of the compound of formula (26) are dissolved in 120.0 parts by volume of dimethyl formamide. 6.4 Parts of sodium methylate and then a solution of 19.5 parts of p-phenylbenzaldehyde in 80.0 parts by volume of dimethyl formamide are slowly added, care being taken to keep the temperature between 25° and 40°. Then the mixture is heated to the boil and stirring is continued for a further hour at the boil.

The reaction mixture is cooled to about 10° and run into a mixture of water and ice. The product settles out and is filtered off with suction, washed well with water and dried. The 4-(5''-methoxylbenzoxazolyl-2'')-4-phenylstilbene of formula (10) is obtained in very good yield.

Application Example A

A fabric of polyester fibre is padded at room temperature with an aqueous dispersion containing, per litre, 0.1 to 0.6 part of one of the compounds of formulae (10) to (13) and 1.0 part of an adduct of about 8 moles of ethylene oxide on 1 mole of p-tert. octylphenol. The fabric is expressed to retain 80 % of its weight of the dispersion, dried for 30 minutes at 60° and submitted to dry heat treatment at 130° to 220° for a few seconds to 1 minute in inverse ratio to the temperature. The treated fabric has a very much whiter appearance than the untreated material. The method of this example can be employed with a polyester blend fabric, e.g. polyester/cotton, in place of 100 % polyester fabric, which is brightened to the same extent as the latter material.

Application Example B

In melt spinning equipment 200.0 parts of polyethylene terephthalate are melted at 280° under a nitrogen atmosphere. 0.04 Part of the compound of formula (10) is added, which also melts at this temperature and on stirring blends homogeneously with the polymer. 4 Parts of titanium dioxide are added as delustrant, with continued stirring for homogeneous blending. The melt is extruded as filaments, which are cooled by passing through a water jet, cold drawn and wound in the normal bobbin form.

Products made of polyester filaments brightened by this method exhibit a much more intense white than comparable products of polyester filament without the incorporated brightener.

In place of the compound of formula (10) one of the compounds of formulae (11) to (13) or (19) to (22) can be employed, which produce white effects of similar intensity.

Application Example C 500.0 Parts of polyamide chips synthesized from ε-caprolactam, 1.5 parts of titanium dioxide and 0.1 part of the compound of formula (10) are intimately mixed in a mixer. The mixture is melted in an autoclave at 250°–260° in the absence of oxygen and the melt extruded as filaments with the aid of nitrogen. After cooling the filaments are drawn to 400 % of the initial length and wound on bobbins. Polyamide fibres thus produced show a notably high degree of whiteness.

In place of the compound of formula (10) one of formula (11) or (20) can be employed with equally good success.

Application Example D

A charge of polypropylene granules delustered with titanium dioxide is mixed with 0.01–0.05 % of its weight of the compound of formula (10) in a tumbler mixer. The granules with the absorbed brightener are melted in a spinning machine under a nitrogen atmosphere and spun at 310° as filaments, which are hot drawn in a two-stage process. The filaments exhibit a superior degree of whiteness to comparable filaments produced without brightener. White effects of similar quality are obtained when in this Example the compounds of formulae (11) to (13) or (20) to (22) are used in place of the one of formula (10).

Application Example E

A solution of 200.0 parts of polyvinyl chloride and 0.04 part of the compound of formula (10) in methylene chloride is spun by the wet spinning process. The brilliant white filaments show good light fastness. The compounds of formulae (11) to (13) and (20) to (22) are equally as good as that of (10) for this application.

Application Example F 200.0 Parts of polypropylene granules are dry coated with 0.04 part of the compound of formula (10) in a mixer. The granules are processed on a roller mill at 140°–220° and either injection moulded directly as tiles or panels, or regranulated and converted into other injection moulded goods. The moulded goods show decidedly superior whiteness to similar goods without a brightener additive.

In place of the compound of formula (10), one of the compounds of formulae (11) to (13) or (20) to (22) can be employed to give similar white effects.

Application Example G

A charge of 100.0 parts of polyester granules is dry coated in a tumbler mixer with 0.02 part of the compound of formula (10) and injection moulded. The moulded products are superior in appearance to products containing no optical brightener. If the granulated polyester is replaced by other materials in granule form, such as polyamide, polystyrene, polyethylene or secondary cellulose acetate, the resulting products display a comparable degree of brightening. The same is true when instead of the compound of formula (10) one of the compounds of formulae (11) to (13) or (19) to (22) is employed.

Application Example H 100.0 Parts of a polyvinyl chloride moulding composition consisting of 65 parts of polyvinyl chloride, 35 parts of plasticizer, e.g. dioctyl phthalate, and 2 % of a stabilizer on the weight of the polyvinyl chloride is mixed with 0.01–0.05 part of one of the compounds of formulae (10) to (13) or (20) to (22). The mixture is processed on a roller mill for 3–6 minutes at 165°–185° and drawn off as film. If opaque film is desired, 2.5% titanium dioxide is mixed with the other components prior to processing.

Polyvinyl chloride films produced in this way are of superior appearance to comparable films without a brightener addition.

Having thus disclosed the invention what we claim is:

1. A monobenzoxazolylstilbene of the formula

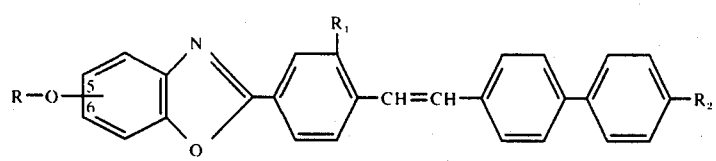

wherein
R—O is lower alkoxy and stands in one of the positions 5 or 6,
$R_1$ is hydrogen or lower alkyl, and
$R_2$ is hydrogen, chlorine or lower alkyl.

2. A monobenzoxazolylstilbene according to claim 1 of formula

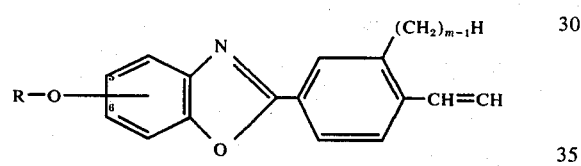

-continued

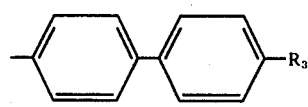

wherein
R—O is lower alkoxy and stands in one of the positions 5 or 6,
$R_3$ is hydrogen, chlorine or methyl and
$m$ is 1 or 2.

3. The monobenzoxazolylstilbene according to claim 1 of formula

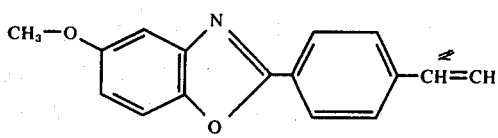

4. The monobenzoxazolylstilbene according to claim 1 of formula

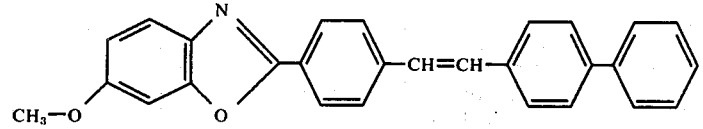

5. The monobenzoxazolylstilbene according to claim 1 of formula

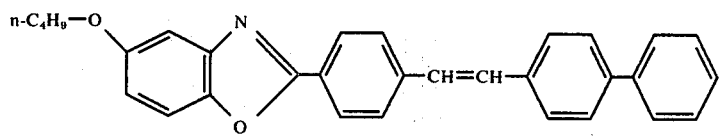

6. The monobenzoxazolylstilbene according to claim 1 of formula

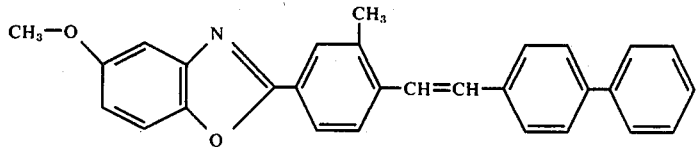

7. The monobenzoxazolylstilbene according to claim 1 of formula

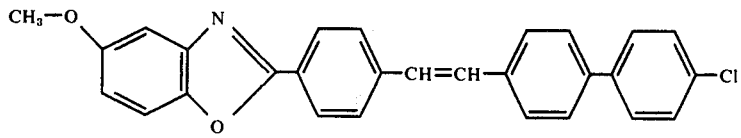

* * * * *